(12) United States Patent
Miller et al.

(10) Patent No.: US 11,783,475 B2
(45) Date of Patent: Oct. 10, 2023

(54) IN EAR DEVICE CUSTOMIZATION USING MACHINE LEARNING

(71) Applicant: Meta Platforms Technologies, LLC, Menlo Park, CA (US)

(72) Inventors: Antonio John Miller, Woodinville, WA (US); Morteza Khaleghimeybodi, Bothell, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 261 days.

(21) Appl. No.: 16/785,386

(22) Filed: Feb. 7, 2020

(65) Prior Publication Data
US 2021/0248737 A1 Aug. 12, 2021

(51) Int. Cl.
| | | |
|---|---|---|
| *G06T 7/00* | (2017.01) | |
| *G06T 7/13* | (2017.01) | |
| *H04S 7/00* | (2006.01) | |
| *B29C 64/10* | (2017.01) | |
| *G06N 20/00* | (2019.01) | |
| *A61B 5/107* | (2006.01) | |
| *B33Y 10/00* | (2015.01) | |
| *B33Y 50/02* | (2015.01) | |
| *B33Y 80/00* | (2015.01) | |
| *G06T 19/20* | (2011.01) | |

(52) U.S. Cl.
CPC ............ *G06T 7/0012* (2013.01); *A61B 5/107* (2013.01); *B29C 64/10* (2017.08); *G06N 20/00* (2019.01); *G06T 7/13* (2017.01); *A61B 2562/0204* (2013.01); *B33Y 10/00* (2014.12); *B33Y 50/02* (2014.12); *B33Y 80/00* (2014.12); *G06T 19/20* (2013.01); *G06T 2200/04* (2013.01); *G06T 2200/08* (2013.01); *G06T 2207/20* (2013.01); *G06T 2207/30004* (2013.01)

(58) Field of Classification Search
CPC .......... G06T 7/0012; G06T 7/13; H04S 7/304
See application file for complete search history.

(56) References Cited

U.S. PATENT DOCUMENTS

| | | |
|---|---|---|
| 5,589,895 A | 12/1996 | Mizuno |
| 6,533,418 B1 | 3/2003 | Izumitani et al. |
(Continued)

FOREIGN PATENT DOCUMENTS

| | | |
|---|---|---|
| EP | 2905972 A2 | 8/2015 |
| WO | WO 2019/129709 A1 | 7/2019 |

OTHER PUBLICATIONS

PCT International Search Report and Written Opinion, PCT Application No. PCT/US2020/067054, dated Mar. 22, 2021, 13 pages.
(Continued)

*Primary Examiner* — Yl Yang
(74) *Attorney, Agent, or Firm* — Fenwick & West LLP

(57) ABSTRACT

A design system generates a design for an in-ear device customized for a user. The in-ear device produces audio content for the user. The design system captures anthropometric data of the user. Using machine learning techniques, the design system determines features of an ear of the user from the anthropometric and generates a three dimensional (3D) geometry of the user's ear. A design for the in-ear device is generated based on the 3D geometry of the user's ear and includes a shell configured to fit in at least a portion of an ear canal of the user.

21 Claims, 8 Drawing Sheets

(56) References Cited

U.S. PATENT DOCUMENTS

| | | | |
|---|---|---|---|
| 10,880,667 | B1 | 12/2020 | Cho et al. |
| 2001/0024262 | A1 | 9/2001 | Kim |
| 2003/0074174 | A1* | 4/2003 | Fu .................... B33Y 80/00 703/13 |
| 2004/0130674 | A1 | 7/2004 | Epstein |
| 2012/0033178 | A1 | 2/2012 | Chauveau et al. |
| 2013/0239301 | A1* | 9/2013 | Broderick ............... A42C 5/04 2/171.2 |
| 2014/0268007 | A1 | 9/2014 | Ben-Shahar |
| 2015/0110349 | A1* | 4/2015 | Feng ................... G06V 40/162 382/103 |
| 2015/0154678 | A1 | 6/2015 | Fonte et al. |
| 2015/0154679 | A1 | 6/2015 | Fonte et al. |
| 2016/0299360 | A1 | 10/2016 | Fonte et al. |
| 2017/0272890 | A1* | 9/2017 | Oh .......................... H04S 7/304 |
| 2018/0054604 | A1* | 2/2018 | Boyd ................... H04N 13/128 |
| 2018/0081200 | A1 | 3/2018 | Giordanetti |
| 2018/0218198 | A1* | 8/2018 | Hushchyn ............ G06V 40/165 |
| 2020/0215415 | A1 | 7/2020 | Bologna et al. |
| 2020/0336858 | A1 | 10/2020 | Brimijoin et al. |

OTHER PUBLICATIONS

United States Office Action, U.S. Appl. No. 16/785,391, filed May 27, 2021, 16 pages.

United States Office Action, U.S. Appl. No. 16/785,391, filed Apr. 1, 2021, 15 pages.

International Preliminary Report on Patentability for International Application No. PCT/US2020/067054, dated Aug. 18, 2022, 11 pages.

Non-Final Office Action dated Aug. 5, 2022 for U.S. Appl. No. 17/500,781, filed Oct. 13, 2021, 18 pages.

Achlioptas P., et al., "Learning Representations and Generative Models for 3D Point Clouds," arXiv preprint arXiv:1707.02392v2, Dec. 5, 2017, 22 pages.

Besl P.J., et al., "A Method for Registration of 3-D Shapes," IEEE Transactions on Pattern Analysis and Machine Intelligence, Feb. 1992, vol. 14, No. 2, pp. 239-256.

Dai H., et al., "A Data-Augmented 3D Morphable Model of the Ear," 2018 13th IEEE International Conference on Automatic Face & Gesture Recognition (FG 2018), May 15, 2018, 5 pages.

Egger B, "3D Morphable Face Models-Past, Present, and Future," ACM Transactions on Graphics. Jun. 2020, vol. 39, No. 5, 38 pages.

Ghosh P., et al., "GIF: Generative Interpretable Faces," 2020 International Conference on 3D Vision (3DV), Nov. 25, 2020, 12 pages.

Gower J.C., "Generalized Procrustes Analysis," Psychometrika, Mar. 1975, vol. 40, pp. 33-51, Retrieved from the Internet URL: https://econpapers.repec.org/article/sprpsycho/.

Groueix T., "A Papier-Mâché Approach to Learning 3D Surface Generation," Proceedings of the IEEE Conference on Computer Vision and Pattern Recognition (CVPR), Jun. 18-23, 2018, 9 pages.

Jolliffe I., "Principal Component Analysis," International Encyclopedia of Statistical Science—Springer, 2011, pp. 1094-1096.

Kazhdan M., et al., "Rotation Invariant Spherical Harmonic Representation of 3D Shape Descriptors," Proceedings of the 2003 Eurographics/ACM SIGGRAPH Symposium on Geometry Processing, 2003, pp. 156-164.

Li Y., et al., "PointCNN: Convolution On X-Transformed Points," Advances in Neural Information Processing Systems, 2018, Retrieved from the Internet: URL: https://proceedings.neurips.cc/paper/2018/file/f5f8590cd58a54e94377e6ae2eded4d9-Paper.pdf.

Mursalin M., "3D Morphable Ear Model: A Complete Pipeline from Ear Segmentation to Statistical Modeling," 2021 Digital Image Computing: Techniques and Applications (DICTA), IEEE, Nov. 29, 2021, pp. 1-6.

Ploumpis S., et al., "Combining 3D Morphable Models: A Large Scale Face-And-Head Model," Proceedings of the IEEE/CVF Conference on Computer Vision and Pattern Recognition (CVPR), pp. 10934-10943.

Ploumpis S., et al., "Towards a Complete 3D Morphable Model of the Human Head," IEEE Transactions on Pattern Analysis and Machine Intelligence, Apr. 29, 2020, vol. 43, No. 11, 18 pages.

Qi C.R., et al., "PointNet++: Deep Hierarchical Feature Learning on Point Sets in a Metric Space", Neural Information Processing Systems (NIPS), 2017, 14 Pages.

Qi C.R., et al., "PointNet: Deep Learning on Point Sets for 3D Classification and Segmentation," In Proceedings of the IEEEE Conference on Computer Vision and Pattern Recognition, Jul. 21-26, 2017, 19 Pages.

Wang N., et al., "Pixel2Mesh: Generating 3D Mesh Models from Single RGB Images," European Conference on Computer Vision (ECCV), 2018, 16 pages.

Wang Y., et al., "Dynamic Graph CNN for Learning on Point Clouds," ACM Transactions on Graphics (TOG), Oct. 10, 2019, vol. 38, No. 5, 12 pages.

Yang G., et al., "PointFlow: 3D Point Cloud Generation with Continuous Normalizing Flows," Proceedings of the IEEE/CVF International Conference on Computer Vision (ICCV), 2019, pp. 4541-4550.

Zhou Y., et al., "Deformable Models of Ears in-the-Wild for Alignment and Recognition," 2017 12th IEEE International Conference on Automatic Face & Gesture Recognition (FG 2017), May 30, 2017, 8 pages.

Zolfaghari R., et al., "Generating a Morphable Model of Ears," 2016 IEEE International Conference on Acoustics, Speech and Signal Processing (ICASSP), Mar. 20, 2016, pp. 1771-1775.

* cited by examiner

IN EAR DEVICE CUSTOMIZATION USING MACHINE LEARNING

FIELD OF THE INVENTION

This disclosure generally relates to using machine learning (ML) to generate three dimensional (3D) geometries, and specifically relates to in-ear device customization based on a 3D geometry of a user's ear.

BACKGROUND

In-ear devices present users with audio content. A standard shape and size of a headset may not fit all users' ears, due to variations in the shape and geometry of users' ears. An ill-fitting in-ear device may feel uncomfortable and/or result in a degraded quality of audio content. In addition, an ill-fitting in-ear device will cause degradation of passive acoustic attenuation that is needed to achieve superior performance, for example for active noise cancellation.

SUMMARY

Machine learning techniques may be used to customize an in-ear device for a user. From anthropometric data (e.g., images of a user's ear), machine learning techniques identify features of an ear of the user and subsequently generate a three-dimensional (3D) geometry of the ear. The 3D geometry of the ear specifies a shape and/or size of the user's ear that may be unique to the user. Accordingly, from the 3D geometry, an in-ear device design is generated that custom fits the user.

In some embodiments, a method generates a design of an in-ear device. The method includes generating a 3D geometry of a user's ear based in part on anthropometric data of the user, the 3D geometry describing a shape of at least a portion of an ear canal of the ear. Based in part on the 3D geometry of the ear, a design of an in-ear device is generated, the design describing a shell of the in-ear device that is customized to fit within at least a portion of the ear canal.

In some embodiments, a system generates a design of an in-ear device. The system includes an imaging device and a controller. The imaging device is configured to capture an image of a user's ear. The controller is configured to generate a 3D geometry of the ear, based in part on anthropometric data of the user from the image of the ear, wherein the 3D geometry describes a shape of at least a portion of an ear canal of the ear. The controller further generates the design of the in-ear device based in part of the 3D geometry of the ear, the design describing a shell of the in-ear device that is customized to fit within at least a portion of the ear-canal.

Figure 1:
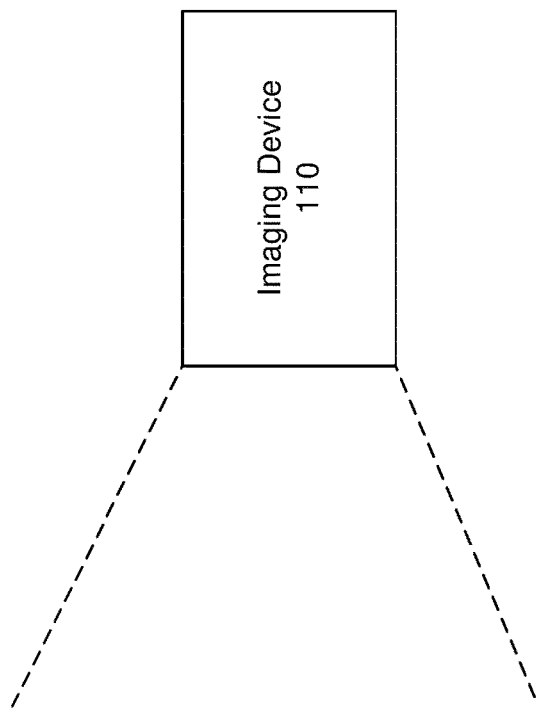
FIG. 1 shows an imaging device capturing an image of a user, in accordance with one or more embodiments.
Figure 1:
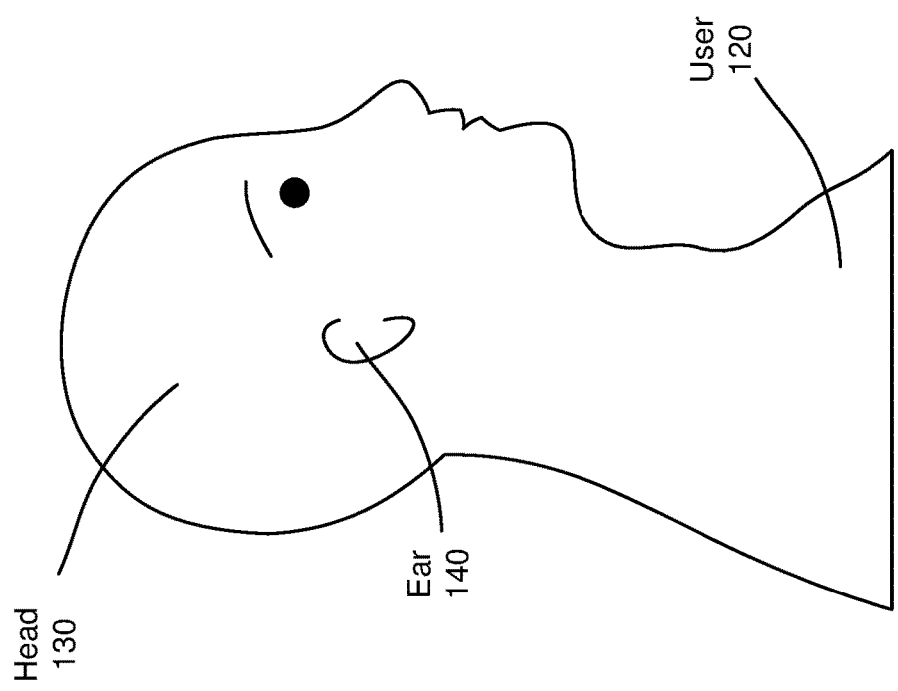

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

A design system generates designs of devices customized for a user. The devices may include an in-ear device and/or an eyewear frame, both configured to present audio content to the user. Conventional in-ear devices and eyewear frames are often available for users in standard sizes for small, medium, and large sized ears and heads, respectively. However, users' features vary greatly even between these standard sizes, which conventional in-ear devices and eyewear frames do not account for. Accordingly, to accommodate variations in size and/or shape of a user's ear and/or head, the design system described herein generates designs of devices customized for the user.

Based on a user's anthropometric data (e.g., images of the user's ear), the design system generates designs for the customized in-ear device and/or eyewear frame. The in-ear device is customized to fit within at least a portion of an ear canal of the user, sealing against the ear canal and/or a portion of a conchal bowl, to better preserve the quality of audio presented via the in-ear device. The eyewear frame is customized to fit the user's head. The frame includes an arm with a coupling element, wherein the coupling element can rotate towards the user's head and/or ears. Accordingly, the customized eyewear frame may fit well on the user's head, ensuring a better audio experience.

The design system generates the customized designs using three-dimensional (3D) geometries of at least portions of the user's head and/or ear that are obtained using a machine learning algorithm that is trained on a plurality of anthropometric data of other users. After receiving anthropometric data of the user, the trained machine learning algorithm generates the 3D geometries of the user's ear and/or the portion of the user's head. The 3D geometries are used to determine design parameters for the in-ear device and/or the eyewear frame. In some embodiments, the in-ear device and/or the eyewear frame may be manufactured from the design parameters and provided to the user. In some embodiments, the in-ear device 360 may comprise two components: a customized shell and a non-custom transducer assembly (i.e. an assembly including acoustic sensors, audio controller, speaker, PCB board, housing and corresponding circuitries), where the customized shell is designed based on the 3D geometry obtained from the trained ML pipeline.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including an HMD connected to a host computer system, a standalone HMD, a mobile device or computing system, or any other hardware platform capable of providing artificial reality content to one or more viewers.

FIG. 1 shows an imaging device 110 capturing one or more images of a user 120, in accordance with one or more embodiments. The imaging device 110 captures one or more images of the user 120, the one or more images including at least a portion of the head 130 (e.g., an ear 140). In some embodiments, the one or more images may be part of a video captured by the imaging device 110. Some or all of the one or more images may be off portions of the head 130 from different angles and/or distances relative to the user 120. The imaging device 110 is a camera, and may be coupled to a device (e.g., a cellphone of the user 120) that is communicatively coupled to a design system. In another embodiment, the imaging device 110 is a component of a headset of the user 120. And in some embodiments, the imaging device 110 is a standalone imaging device, separate from the device. In some embodiments, the imaging device 110 is a depth camera assembly (DCA) that captures depth information about the user 120's head 130 and/or ear 140. In some embodiments, the imaging device 110 is a time of flight camera. For example, the user 120 may take images of themselves from a front facing imaging device 110 of their device. In some embodiments, another user may take the one or more images of the user 120.

Anthropometric data is provided by the device to the design system. Anthropometric data describes a shape of some or all of the head 130. Anthropometric data may include, e.g., one or more images and/or video of the head 130 (e.g., taken by the imaging device 110 or some other imaging device), one or more images and/or video of one or both ears of the user 120 (e.g., taken by the imaging device 110 or some other imaging device), measurements of the head 130, some other data describing a shape of some or all of the head 130, or some combination thereof. For example, an imaging device may be communicatively coupled to the design system. An imaging device may capture the anthropometric data of the user, such as one or more images of the user 120 and provide the data to the design system. The design system subsequently identifies features of the user from the anthropometric data and generates designs of an in-ear device and/or an eyewear frame using the received anthropometric data. The design system generates a 3D geometry of some or all of the head 130 and/or each ear of the user (e.g., the ear 140). And as described below with reference to FIGS. 2 to 6 based on the 3D geometries, customized designs for an in-ear device and/or an eyewear frame are generated for the user 120.

Figure 2:
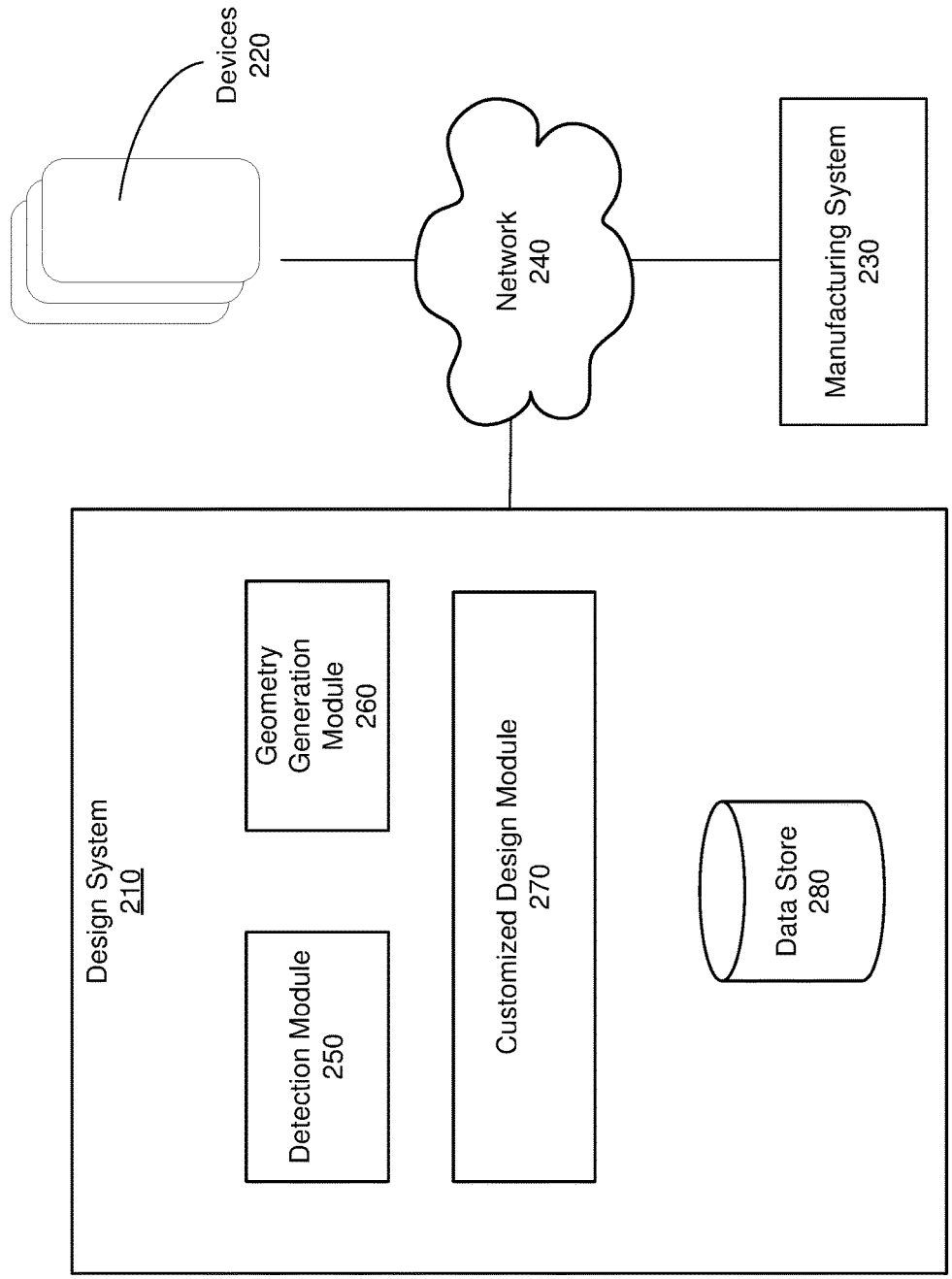
FIG. 2 shows a system environment including a design system, in accordance with one or more embodiments.

FIG. 2 shows a system environment 200 including a design system 210, in accordance with one or more embodiments. The system environment 200 includes the design system 210, one or more devices 220, and a manufacturing system 230. In some embodiments, the design system 210 is communicatively coupled via a network 240 to the one or more devices 220. In some embodiments, the design system 210 is also coupled via the network 240 to the manufacturing system 230. In some embodiments, the system environment 200 includes additional components and/or other components than those described herein.

The one or more devices 220 communicate with the design system 210. Each of the one or more devices 220 are associated with at least one user. A device 220 provides anthropometric data describing a shape of a portion of a target user's head. In some cases, the target user may be the user associated with the device 220. The device 220 may be, e.g., a mobile phone, a laptop, a tablet, a headset (e.g., near-eye display, a head-mounted display), or some other computing device that is communicatively coupled to the design system 210. In some embodiments, one or more of the devices 220 may include an imaging device 110. In some embodiments, the one or more devices 220 may capture the anthropometric data and/or receive the anthropometric data captured by other devices.

The manufacturing system 230 produces the customized in-ear device and/or the customized eyewear frame for the user (e.g., the user 120). In some embodiments, the manufacturing system 230 receives the designs from the design system 210 over the network 240. In some embodiments, the manufacturing system 230 is a part of the design system 210. The manufacturing system 290 is a system that can fabricate an in-ear device and/or a customized eyewear frame. In some embodiments, the manufacturing system 290 may be, e.g., a three-dimensional (3D) printer, an injection molding system, a computer controlled system, some other system that can fabricate an in-ear device and/or a customized eyewear frame, or some combination thereof.

The network 240 couples the design system 210 to the one or more devices 220 and/or to the manufacturing system 230. The network 240 may include any combination of local area and/or wide area networks using both wireless and/or wired communication systems. For example, the network 240 may include the Internet, as well as mobile telephone networks. In one embodiment, the network 240 uses standard communication technologies and/or protocols. Hence, the network 240 may include links using technologies such as Ethernet, 802.11, worldwide interoperability for microwave access (WiMAX), 2G/3G/4G mobile communications protocols, digital subscriber line (DSL), asynchronous transfer mode (ATM), InfiniBand, PCI Express Advanced Switching, etc. Similarly, the networking protocols used on the network 240 can include multiprotocol label switching (MPLS), the transmission control protocol/Internet protocol (TCP/IP), the User Datagram Protocol (UDP), the hypertext transport protocol (HTTP), the simple mail transfer protocol (SMTP), the file transfer protocol (FTP), etc. The data exchanged over the network 240 can be represented using technologies and/or formats including image data in binary form (e.g. Portable Network Graphics (PNG)), hypertext markup language (HTML), extensible markup language (XML), etc. In addition, all or some of links can be encrypted using conventional encryption technologies such as secure sockets layer (SSL), transport layer security (TLS), virtual private networks (VPNs), Internet Protocol security (IPsec), etc.

The design system 210 outputs designs of devices customized for the user. The customized designs include a customized in-ear device and/or a customized eyewear frame. The design system 210 includes a detection module 250, a geometry generation module 260, a customized design module 270, a data store 280. In alternate embodiments, the design system 210 may also include the manufacturing system 230. In some embodiments, the design system 210 may be a component of and/or hosted on one or more of the devices 220 In some embodiments, the design system 210 includes modules other than those shown in FIG. 2. Similarly, in some cases, functions can be distributed among the components in a different manner than is described here.

The detection module 250 detects features of the user (e.g., the user 120) from anthropometric data. The detection module 250 may use machine learning algorithms, edge detection, and/or computer vision to detect features of the user, the features relating to a face and/or a head of the user. For example, the features may be parts of an ear (e.g., the ear 140) and/or a portion of a head (e.g., the head 130).

In some embodiments, the detection module 250 identifies a location of one or more features of the user via image processing and image segmentation. The detection module 250 may use a Canny edge detection algorithm to identify a location of the ear and/or portion of the head. In another embodiment, the detection module 250 may use cascaded AdaBoost classifiers and algorithms to detect and localize an ear within the input images.

In some embodiments, the detection module 250 trains one or more machine learning algorithms to detect features from anthropometric data. The training includes a positive training set and a negative training set. The positive training set includes a plurality of anthropometric data of other users with known features. For example, the plurality of anthropometric data in the positive training set may include a plurality of images of other users, each image including at least one feature in a known location. The negative training dataset includes a plurality of images that do not include known user features.

The detection module 250 applies the trained machine learning algorithm to the user's anthropometric data. In response to receiving anthropometric data of the user, such as one or more images of the user, the machine learning algorithm outputs features of the user. Features of the user describe anatomical characteristics of the user. For example, features of the user may include an ear, a nose, an eyebrow, some other anatomical characteristics, or some combination thereof. The output features may include measurements as well as locations within the anthropometric data of the identified features. For example, the identified features may be of an ear of the user, such as an entrance to an ear canal, a conchal bowl of the ear, and a pinna, among others. In some embodiments, the identified features of the user may also include features of a portion of the user's head, such as a distance from an eye to the pinna, a temple, and a diameter and/or length of the ear. The machine learning technique used may be a cascaded adaptive boosting (AdaBoost) algorithm. Other examples of machine learning techniques include linear support vector machine (linear SVM), neural networks, logistic regression, naïve Bayes, memory-based learning, random forests, bagged trees, decision trees, boosted trees, or boosted stumps, which may be used in different embodiments.

In some embodiments, the detection module 250 uses computer vision techniques to detect features of the user. The computer vision techniques enable the detection module 250 to detect features of the user from a plurality of anthropometric data (e.g., a plurality of images). The plurality of images may be from different angles, in which some features of the user may be occluded (e.g., hair covering an ear of the user in some angles). Accordingly, the detection module 250 detects features of the user from images showing the user from multiple angles, even when the features are occluded in a subset of the images.

The geometry generation module 260 generates a three-dimensional (3D) model of the features of the user from anthropometric data. The 3D model includes features such as the ear of the user and/or a portion of the user head. The geometry generation module 260 may annotate the anthropometric data, such as the one or more images of the user. The annotations may locate and/or describe the features identified by the detection module 250. For example, annotations of an ear of the user may include features of the ear, such as a pinna, an entrance to an ear canal, and/or a conchal bowl of the ear. Annotations of features may further include measurements of the user's ear relative to the user's head, including a distance from the ear to an eye of the user, a length of the ear, and a width of the ear. The length of the ear may be measured from the top surface of the pinna to the ear lobe, whereas the width of the ear may be measured from the side of the pinna to a tragus of the ear. The annotations may include features of the user other than those described herein.

The geometry generation module 260 uses machine learning techniques, such as a convolutional neural network, to generate a 3D geometry (i.e., mesh) of the identified features of the user. In particular, the geometry generation module 230 generates a 3D geometry of the user's ear, as well as a 3D geometry of the portion of the user's head. The mesh comprises key points and edges of the identified features based on the annotated anthropometric data. The geometry generation module 260 is trained on a positive training set and a negative training set. The positive training set includes other users' anthropometric data corresponding to previously generated meshes, such as images of their heads and ears with corresponding 3D geometries. Accordingly, anthropometric data of a user's ear, for example, may correspond to a mesh of a user's ear that delineates a 3D geometry of an ear canal of the user's ear. The negative training set includes anthropometric data for other users that do not include the heads and ears of other users. Accordingly, in response to anthropometric data, such as an image, of the user's ear and/or a portion of the user's head, the geometry generation module 260 outputs a set of key points and detected edges. The key points and detected edges are compiled to form a 3D geometry of the user features captured in the anthropometric data. In some embodiments, the geometry generation module 260 uses a decoder to predict key points that are occluded. For example, a portion of the ear in the image used as input anthropometric data may be occluded by a portion of the user's ear, an earring, and/or a scarf. The geometry generation module 260 creates a shape basis from the detected key points and edges and subsequently generates a 3D reconstructed geometry of the ear.

The customized design module 270 generates a design for devices customized for the user. The customized devices may include an in-ear device and/or an eyewear frame, among others. The designs may be one or more computer aided design and/or graphics documents describing the shapes and specifications of the customized devices.

In some embodiments, the customized design module 270 generates a design for the in-ear device from a 3D geometry of the user ear. As noted above, the generated 3D geometry of the user's ear includes a geometry of the ear canal. The customized design module 270 subsequently generates the design for the in-ear device, the design describing a shell of the in-ear device that fits at least within a portion of the user's ear canal. In some embodiments, the design of the shell is configured to seal against the user's ear canal, thereby preventing the leakage of audio content produced by the in-ear device. In some embodiments, the design specifies that a portion of the shell is also configured to rest and/or seal against the user's conchal bowl, when the in-ear device is placed within the ear canal. The shell is also designed to house components of the in-ear device, such as one or more acoustic sensors, a controller, and a speaker. Some subset of the in-ear device's components within the shell may be standardized across multiple users, whereas in some embodiments, the components are customizable by each user. The customized design module 270 provides, in some embodiments, the design of the in-ear device to the manufacturing system 230.

In some embodiments, the customized design module 270 generates a design for an eyewear frame customized for the user. The eyewear frame produces audio content for the user. The customized design module 270 determines design parameters for a coupling element of the eyewear frame. The coupling element may include a temple and/or a temple tip, each of which may be customized for the user. In some embodiments, at least a portion of the coupling element may be fungible and/or customizable by and/or for the user. For example, the design parameters may specify an angle of rotation of the coupling element. The temple may accordingly shift inwards, towards the user's head, to ensure a customized fit. In some embodiments, the angle of rotation also specifies a bend of the temple tip around the user's ear, thereby preventing the eyewear frame from falling off.

The data store 280 stores data for use by the design system 210. The data stored in the data store 280 may include anthropometric data of users, features of users, designs of the in-ear device and/or eyewear frame, data sets for training the detection module 250 and the geometry generation module 260, the generated 3D geometries of the user, other data relevant for use by the design system 210, or some combination thereof.

Figure 3A:
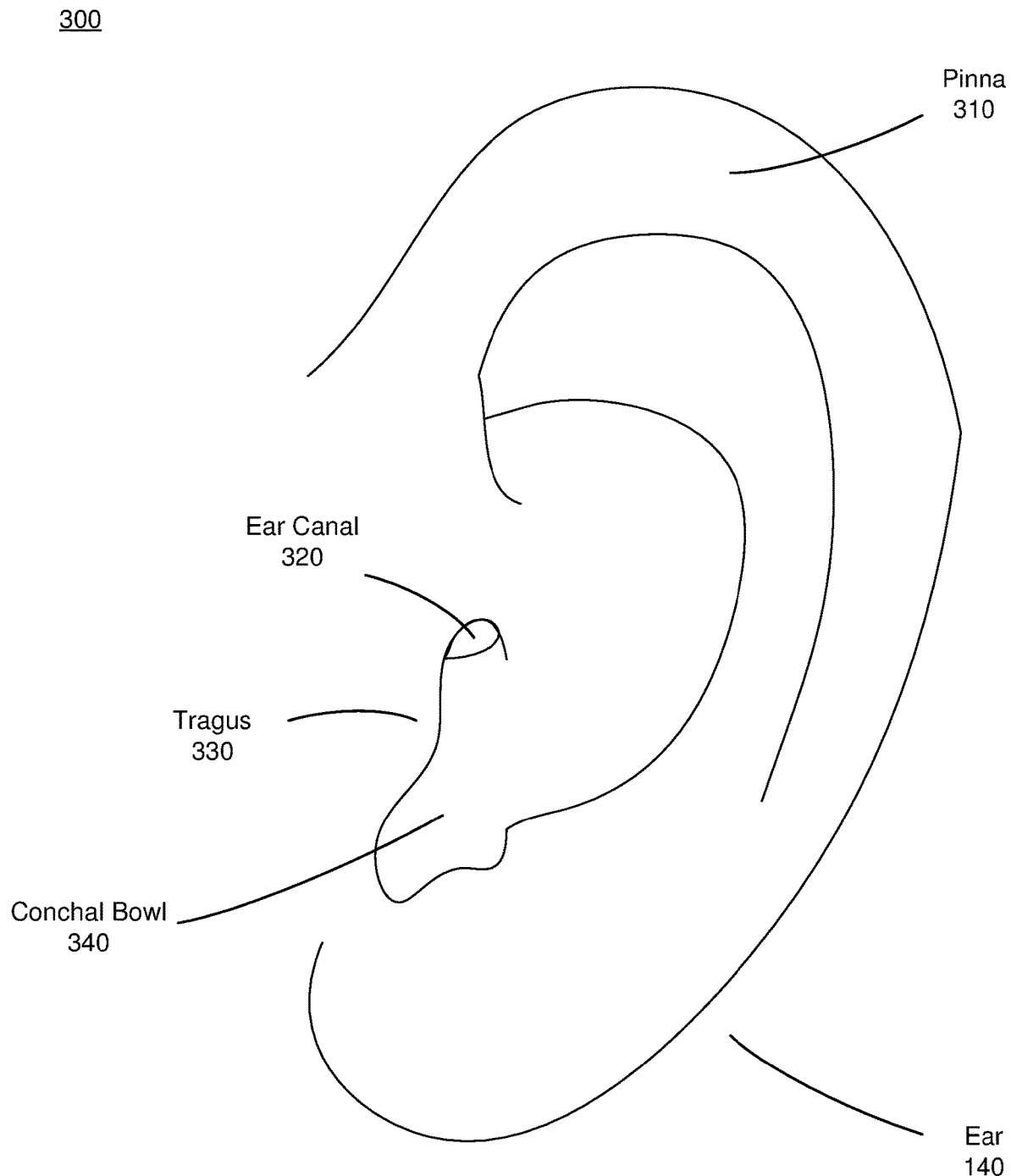
FIG. 3A shows a view of an ear of the user, in accordance with one or more embodiments.

FIG. 3A shows the ear 140 of the user 120, in accordance with one or more embodiments. Anthropometric data (e.g., images, measurements, etc.) describing the ear 140 are used by a design system to generate a design for a customized in-ear device for the user 120. The ear 140 includes features such as a pinna 310, an entrance to an ear canal 320, a tragus 330, a conchal bowl 340, or some combination thereof. The ear 140 includes features other than those described herein.

The imaging device 110, as described in FIG. 1, may capture the anthropometric data of the ear 140. A machine learning algorithm of the design system may identify features of the ear 140 from the anthropometric data. The machine learning algorithm generates a 3D geometry of the ear 140. The machine learning algorithm may be trained on a plurality of anthropometric data of other users' ears.

Figure 3B:
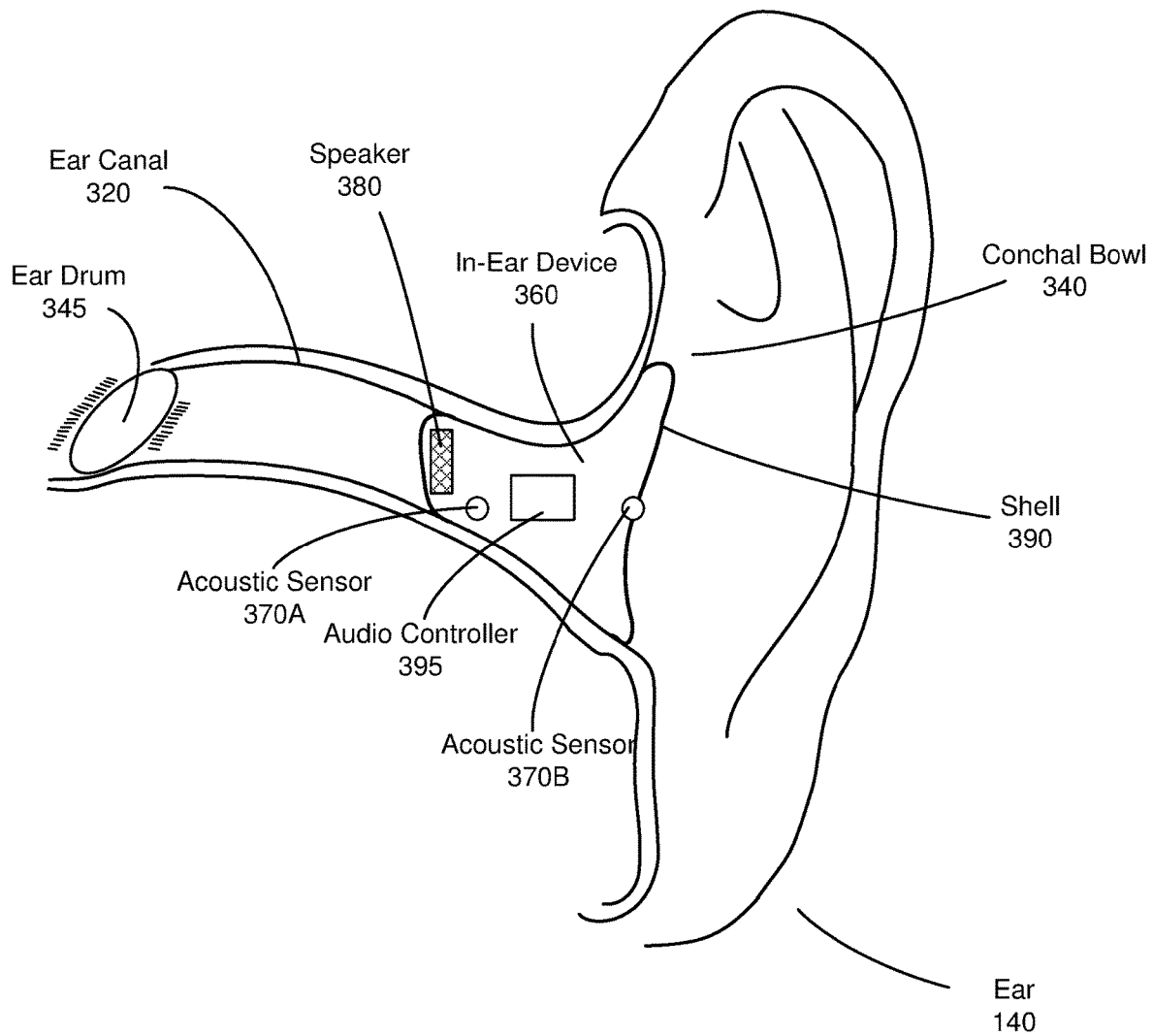
FIG. 3B shows a cross-sectional view of an ear including an in-ear device, in accordance with one or more embodiments.

FIG. 3B shows a cross-sectional view 350 of the ear 140 including an in-ear device 360, in accordance with one or more embodiments. The in-ear device 360, customized to fit within the ear 140, presents audio content to a user (e.g., the user 120). The cross-sectional view 350 includes the ear canal 320, the conchal bowl 340, an ear drum 345, and the in-ear device 360. The in-ear device 360 presents audio content to the user. A portion of the in-ear device 360 fits within a portion of the ear canal 320 and/or fits against a portion of the conchal bowl 340. The in-ear device 360 includes acoustic sensors 370A, 370B, a speaker 380, a shell 390, and an audio controller 395. In some embodiments, the in-ear device 360 may be communicatively coupled to a headset and/or include additional components than those described herein.

The acoustic sensors 370A, 370B monitor and detect sound. The acoustic sensor 370A may detect sound from a local area around the user 120 and sound transmitted via tissue conduction. For example, in addition to the in-ear device 360, the user 120 may be wearing a headset with an audio system that provides audio content via tissue conduction. Accordingly, the acoustic sensor 370A may detect acoustic content generated by vibrations to tissue in and/or around the ear 140 of the user 120. The acoustic sensor 370B may detect sound from the local area. In some embodiments, the acoustic sensor 370B couples to the shell 390, such that it is unoccluded and detects sound from the local area around the user 120. The acoustic sensors 370A, 370B may be microphones and/or accelerometers, for example. The acoustic sensors 370A, 370B transmit acoustic data to the audio controller 395.

The speaker 380 presents audio content to the user 120 as per instructions from the audio controller 395. In some embodiments, the speaker 380 presents audio content via air conduction, wherein the speaker 380 creates and transmits airborne acoustic pressure waves to the ear drum 345. The ear drum 345's vibrations are detected as sound by a cochlea of the ear 140. In other embodiments, the speaker 380 presents audio content via tissue conduction, wherein vibrations of tissue in and/or around the ear pass through a middle ear ossicular chain of the ear 140 to the cochlea.

The shell 390 houses the components of the in-ear device 360. The design of the shell 390, produced by the design system, is customized for the ear 140 of the user 120. The shell 390 is configured to seal against the ear canal 320. As seen in FIG. 3B, a portion of the shell 390 extends to and seals against a portion of the conchal bowl 340 of the ear 140 as well. In some embodiments, the shell 390 is customized to one or both of a portion of the user 120's ear canal 320 and a portion of the user 120's conchal bowl 340. Accordingly, the customized shell 390 reduces leakage of audio content presented by the speaker 380. To achieve hearthrough capabilities, the shell 390 provides appropriate passive attenuation (i.e., attenuation of the sounds from the environment to the acoustic sensor 370A). The in-ear device 360 may also feel more comfortable for the user 120. The design of the shell 390 may specify that the shell 390 be composed of foam, silicone, plastic, rubber, or some combination thereof. In some embodiments, the design system provides the design of the shell 390 to a manufacturer of the in-ear device 360.

In some embodiments, a subset of the components within the shell 390 of the in-ear device 360 may each be customized for the user 120. For example, the in-ear device 360 for the user 120 may include two acoustic sensors and one speaker within the in-ear device 360, while another user's in-ear device may include one acoustic sensor and one speaker. In another embodiment, the components of in-ear device 360 may be standard across a plurality of in-ear devices, such that all users' in-ear devices have substantially similar components.

The audio controller 395 receives and processes sound detected by the acoustic sensors 370A, 370B, and instructs the speaker 380 to play audio content. The audio controller 395 may instruct the speaker 380 to play audio content based on sound detected by the acoustic sensors 370A, 370B. For example, the audio controller 395 may amplify, attenuate, and/or augment sound from the local area. In some embodiments, the audio controller 395 couples to the headset of the user 120 and instructs the speaker 380 to play audio content corresponding to visual content presented to the user 120.

Figure 4A:
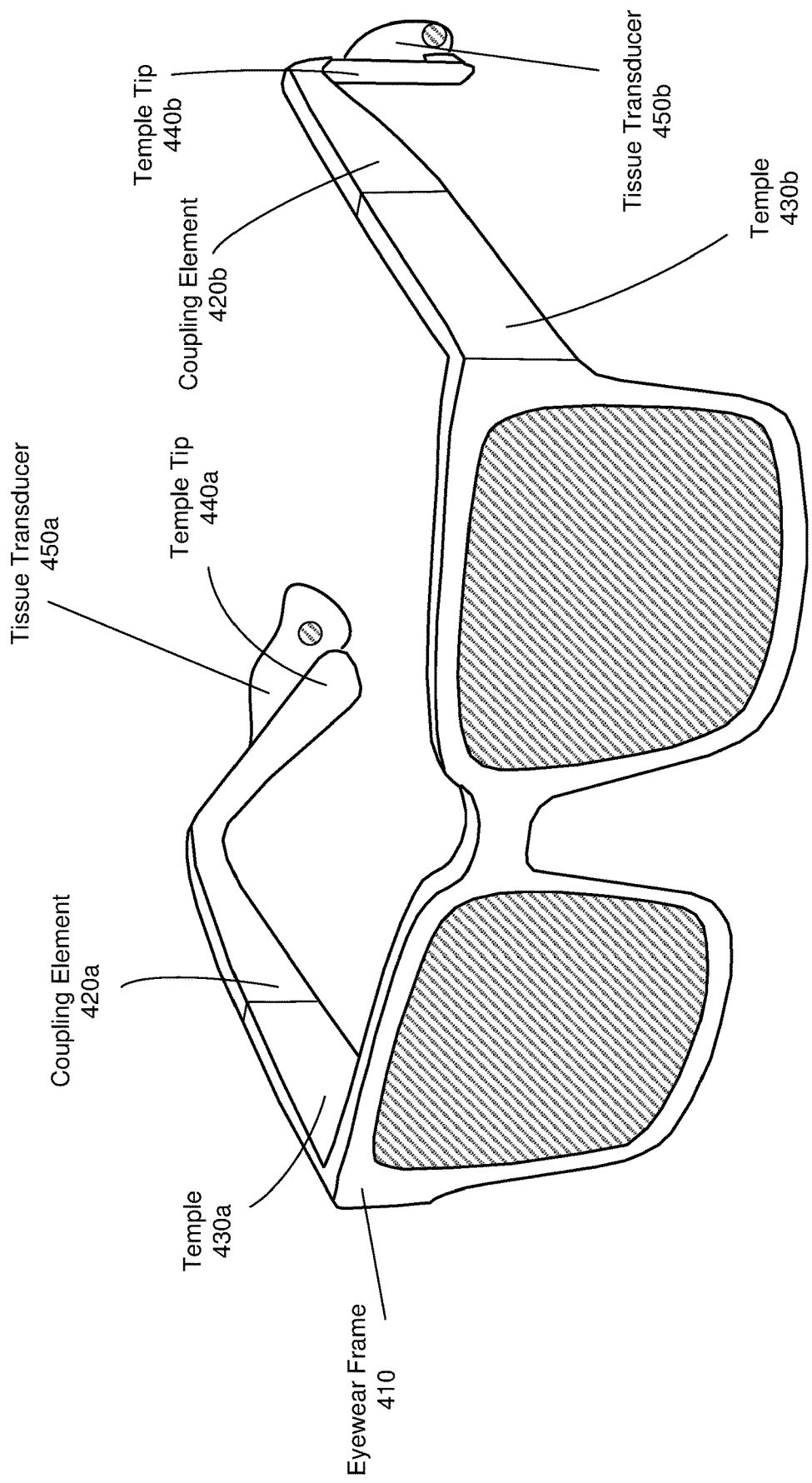
FIG. 4A shows an eyewear frame including coupling elements, in accordance with one or more embodiments.

FIG. 4A shows an eyewear frame 410 including coupling element 420a and 420b, in accordance with one or more embodiments. The eyewear frame 410 provides audio content, and in some embodiments, video content to the user 120. In addition to the coupling elements 420a and 410b, the eyewear frame 410 includes temples 430a and 430b, temple tips 440a and 440b, and tissue transducers 450a and 450b. The eyewear frame 410 may be customized to the user 120's head by a design system, based on anthropometric data of the user 120, as shown in FIG. 1. The eyewear frame 410 may include other features than those described herein, such as a display element and/or corrective lenses.

A coupling element (e.g., 420a) couples a temple (e.g., 430a) to a temple tip (e.g., the temple tip 440a). Each coupling element 420a, 420b may be customized to fit the head 130 of the user 120 by rotating towards the head 130 and/or around user's ears (e.g., the ear 140). The coupling elements 420a, 420b may be customized for the head 130 of the user 120 as per a 3D geometry of a portion of the head 130, output by the design system. The machine learning algorithm generates a 3D geometry of the portion of the head 130. The design system, based on the output 3D geometry of the portion of the head 130, generates design parameters for one or both of the coupling elements 420a, 420b. The design parameters may include a respective length for one or both of the coupling elements 420a, 420b, a respective angle of rotation for one or both of the coupling elements 420a, 420b towards the head 130, and/or a respective angle of rotation for one or both of the coupling element 420a, 420b around the ear. The coupling element 420a, 420b may include and/or couple to at least one of the temples 430a, 430b and the temple tips 440a, 440b. The temples 430a, 430b each couple to an arm of the eyewear frame 410. The temple tip 440a secures the eyewear frame 410 around the ear 140a of the user 120, for example.

The tissue transducers 450a, 450b are configured to present audio content to the user 120 via tissue and/or bone conduction. The tissue transducers 450a, 450b may couple to the head 130 of the user, such as tissue behind the ears (e.g., the ear 140), and directly vibrate bone and/or cartilage to generate the audio content. In some embodiments, the in-ear device 360 may additionally provide audio content to the user 120.

Figure 4B:
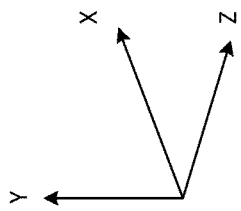
FIGS. 4B and 4C show a portion of the eyewear frame of 4A, in accordance with one or more embodiments.
Figure 4B:
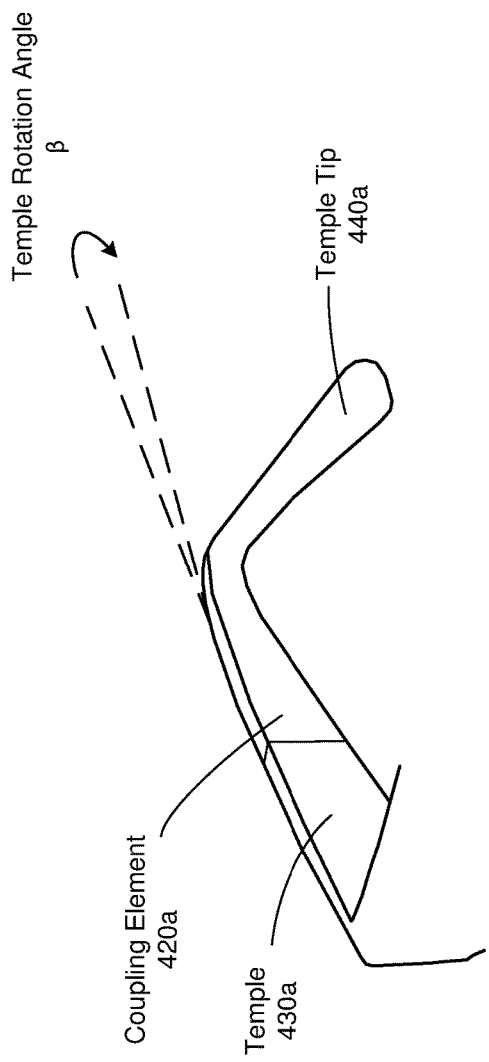
Figure 4C:
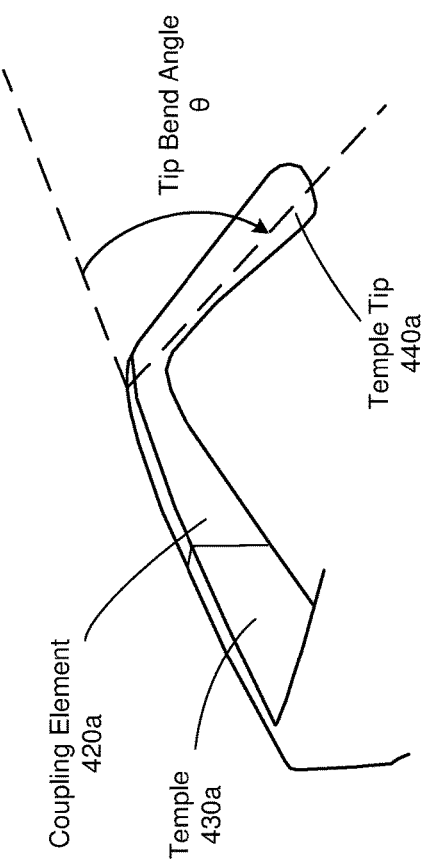

FIGS. 4B and 4C show a portion of the eyewear frame of 4A, in accordance with one or more embodiments. The coupling element 420a may be customized for the user 120 as per the design system's design parameters. The coupling element 420a may couple to and/or include the temple 430a and the temple tip 440a.

In FIG. 4B, the coupling element 420a may rotate by a temple rotation angle β. The temple 430a may be rotated towards the head 130 of the user 120 as per the temple rotation angle β. The temple rotation angle β is a rotation about the y axis. In other embodiments, the temple 430 may rotate about other axes as well. Accordingly, an arm of the eyewear frame may fit better against the head 130 of the user 120. The temple rotation angle β may be included in the design parameters determined by the design system. A plurality of users may have varying temple rotation angles β.

In FIG. 4C, the coupling element 420a may bend by a tip bend angle θ. The temple tip 440a may rotate as per the tip bend angle to curve around the ear 140 of the user 120. Accordingly, the temple tip 440a secures the eyewear frame to the head 130 of the user 120. The tip bend angle θ is a rotation about the z axis, but in other embodiments, may rotate about other axes as well, in other embodiments. The tip bend angle θ may be included in the design parameters determined by the design system, and a plurality of users may have varying tip bend angles θ.

Thus, the customized coupling element 420a contributes to a custom fit of the eyewear frame 410 to the user 120.

Figure 4D:
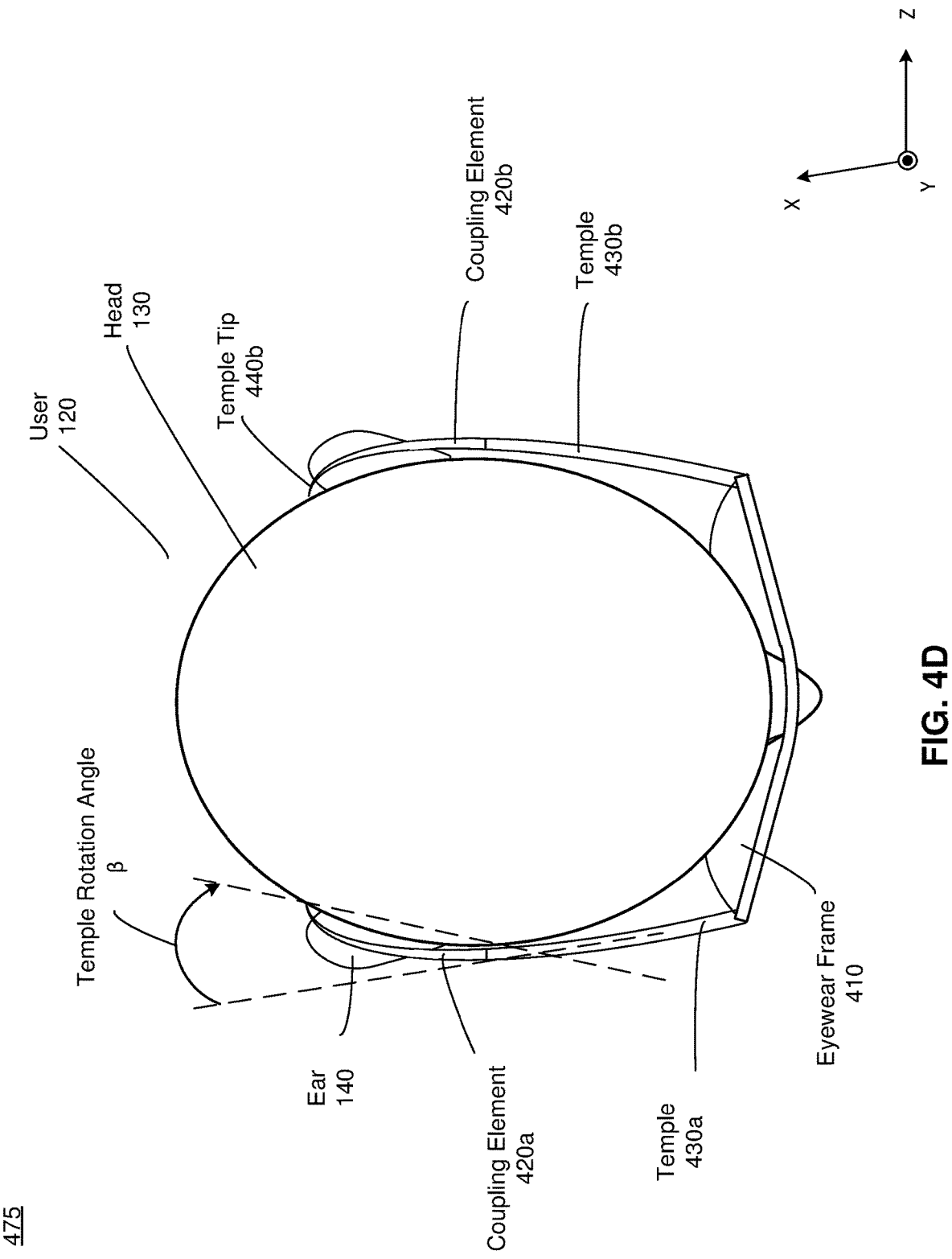
FIG. 4D shows a top-down view of a user wearing the eyewear frame of 4A, in accordance with one or more embodiments.

FIG. 4D shows a top-down view 475 of a user wearing the eyewear frame of 4A, in accordance with one or more embodiments. The top-down view 475 includes the user 120, with the head 130, and the ear 140, wearing the eyewear frame 410. The eyewear frame 410, customized to the user 120, include the coupling elements 420, 420b, the temples 430a, 430b, and the temple tips 440a, 440b. The coupling element 420a is rotated towards the head 130 of the user by the temple rotation angle R at the ear 140 and the temple tip 440a curves around the ear 140 by the tip bend angle θ (not pictured in FIG. 4D). The temple rotation angle R and the tip bend angle θ may be inverted for the other ear of the user 120, such that when anthropometric data of both ears of the user 120 are unavailable, customization along the other coupling element 420b may be reflected along a central axis of the head 130.

Figure 5:
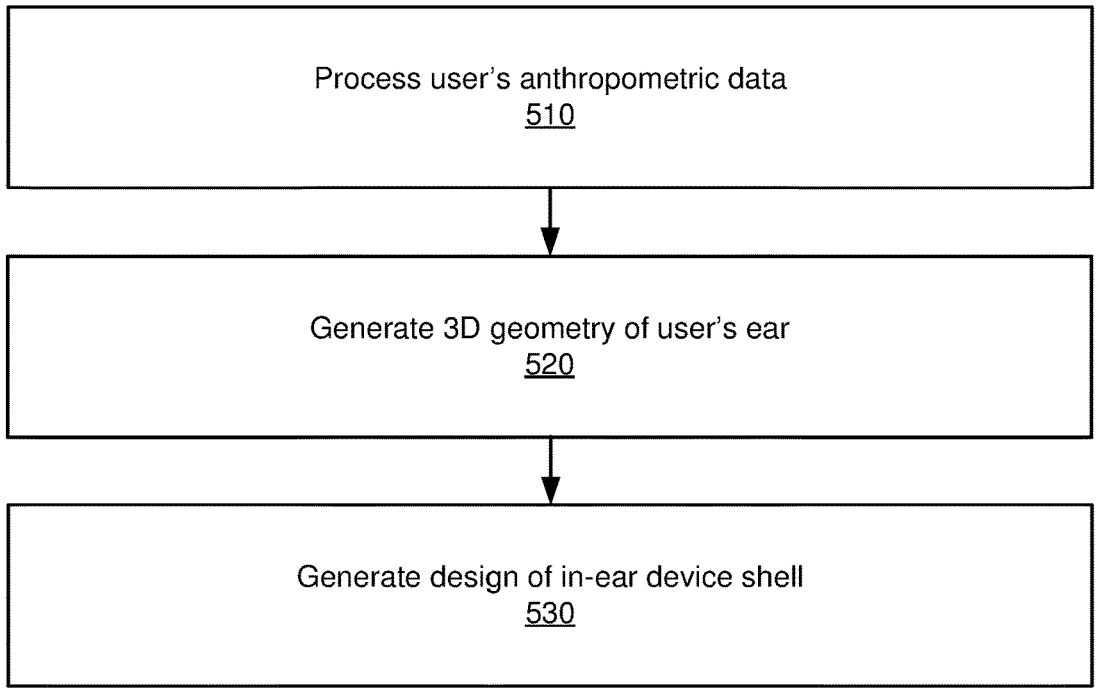
FIG. 5 is a process for generating a design of a customized in-ear device, in accordance with one or more embodiments.

FIG. 5 is a process 500 for generating a design of a customized in-ear device, in accordance with one or more embodiments. The process shown in FIG. 5 may be performed by components of a design system (e.g., the design system 210). Other entities may perform some or all of the steps in FIG. 5 in other embodiments. Embodiments may include different and/or additional steps, or perform the steps in different orders.

The design system processes 510 anthropometric data of a user (e.g., the user 120). In some embodiments, the anthropometric data is one more images of the user. The images may be captured by a device, such as an artificial reality (AR)/virtual reality (VR) headset and/or a client device, such as a mobile phone. In some embodiments, the anthropometric data may be extracted from a captured video of the user. The anthropometric data includes an ear of the user. The design system detects features of the user from the anthropometric data using machine learning techniques and/or edge detection. For example, features of the ear include a pinna, a conchal bowl, and an entrance to an ear canal of the user.

The design system generates 520 a 3D geometry of the user's ear. The 3D geometry is based on the detected features of the ear and is generated by machine learning techniques such as convolutional neural networks. The machine learning model that generates the 3D geometry is trained on a plurality of images of other users' ears. The 3D geometry may describe a portion of the user's ear canal.

The design system generates 530 a design of the in-ear device. The design of the in-ear device includes a shell, wherein a portion of the shell is customized to fit within a portion of the user's ear canal. The design system generates the design from the generated 3D geometry. In some embodiments, the design of the in-ear device also includes circuitry configured to produce audio content. The circuitry is configured to fit within the shell and in some embodiments, may be customized for and/or by the user.

Figure 6:
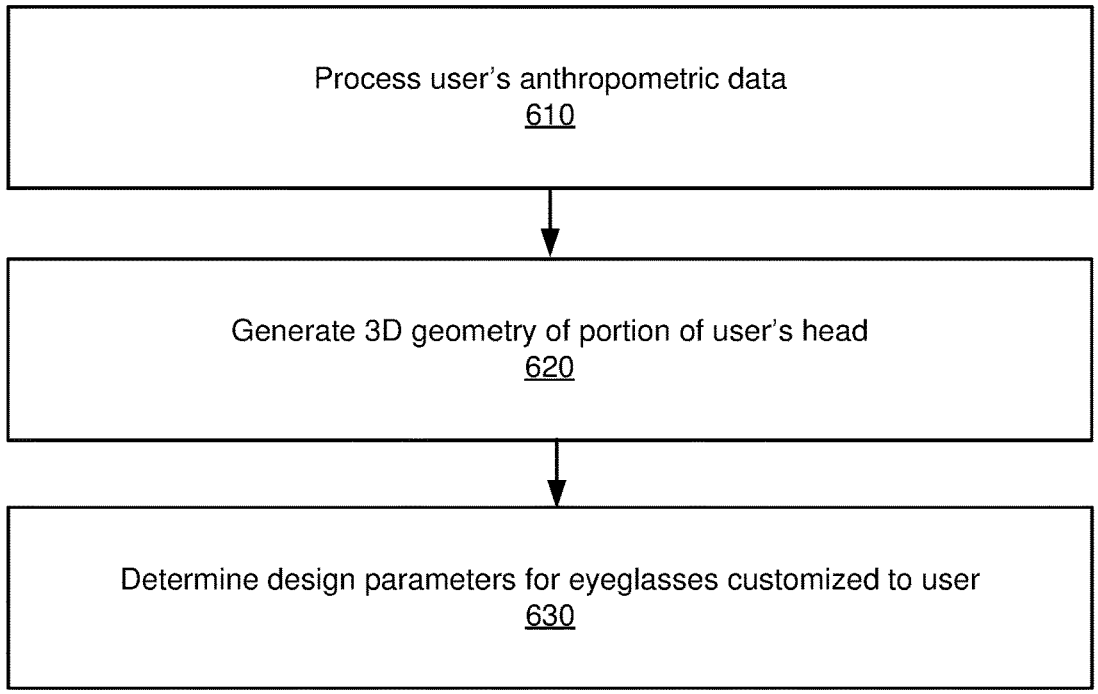
FIG. 6 is a process for generating a design of a customized eyewear frame, in accordance with one or more embodiments.

FIG. 6 is a process 600 for generating a design of a customized eyewear frame, in accordance with one or more embodiments. The process shown in FIG. 6 may be performed by components of a design system (e.g., the design system 210). Other entities may perform some or all of the steps in FIG. 6 in other embodiments. Embodiments may include different and/or additional steps, or perform the steps in different orders.

The design system processes 610 anthropometric data of a user (e.g., the user 120). As described in FIG. 6, anthropometric data may be one or more images of the user, the images including at least a portion of the user's head. In some embodiments, the one or more images are captured by an imaging device, such as an artificial reality (AR)/virtual reality (VR) headset and/or a client device, such as a mobile phone. In some embodiments, the captured anthropometric data may be extracted from a captured video of the user. The design system locates features of the user from the anthropometric data using machine learning techniques and/or edge detection. For example, the design system may determine and locate features such as a distance of the ear from an eye of the user and a size of the ear.

The design system generates 620 a 3D geometry of the features of the user. The 3D geometry is generated by machine learning techniques such as convolutional neural networks. The machine learning model that generates the 3D geometry is trained on a plurality of images of other users' heads and ears.

The design system generates 630 design parameters for the customized eyewear frame. The design parameters are customized to the user and describe a coupling element that interfaces with the eyewear. The coupling element includes a customized end of a temple that includes a temple tip.

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A method comprising:
   storing a training set including anthropometric data of a plurality of different users, the anthropometric data for each of the plurality of different users comprising an image of ears of a given user from the plurality of users and a corresponding three-dimensional (3D) geometry of the ears of the given user that describes shapes of external portions of the ears and portions of ear canals of the given user;
   training a machine learning algorithm using the training set including the anthropometric data of the plurality of users, the trained machine learning algorithm configured to generate 3D geometries of ears;
   receiving anthropometric data of an ear of a user, the anthropometric data including at least one image describing an external portion of the ear of the user;
   generating a 3D geometry of the ear of the user by applying the anthropometric data of the ear of the user that describes the external portion of the ear of the user to the trained machine learning algorithm, wherein the generated 3D geometry describes a shape of at least a portion of an ear canal of the ear of the user; and
   generating a design of an in-ear device based in part on the generated 3D geometry of the ear of the user, the design describing a shell of the in-ear device that is customized to fit within at least a portion of the ear canal of the user.

2. The method of claim 1, further comprising:
   detecting, based on the anthropometric data of the user, features of the ear of the user; and
   generating, based on the features of the ear of the user, the 3D geometry of the ear of the user.

3. The method of claim 2, wherein the features of the ear of the user include at least one of an entrance of the ear canal of the user, a conchal bowl of the ear of the user, and a pinna of the ear of the user.

4. The method of claim 1, wherein generating the 3D geometry of the ear of the user comprises:
   determining features describing the ear of the user using the anthropometric data of the user;
   identifying key points and detected edges describing the ear of the user using the machine learning algorithm and the features; and
   forming the 3D geometry of the ear of the user based in part on the key points and the detected edges.

5. The method of claim 4, further comprising:
predicting key points for a portion of the ear of the user that is occluded;
creating a shape basis for the portion of the ear of the user using the detected key points; and
wherein forming the 3D geometry of the ear of the user is based in part on the shape basis.

6. The method of claim 1, wherein at least a portion of the shell of the in-ear device is configured to seal against the ear canal.

7. The method of claim 1, wherein the shell of the in-ear device houses a speaker and two acoustic sensors.

8. The method of claim 1, wherein the design of the in-ear device is provided to a manufacturer of the in-ear device.

9. The method of claim 1, wherein the anthropometric data includes measurements of the ear of the user, and the measurements are used to generate the 3D geometry of the ear of the user.

10. The method of claim 1, wherein the anthropometric data is an image of the ear of the user received from a device, and the image is used to generate the 3D geometry of the ear of the user.

11. The method of claim 1, wherein the anthropometric data describing the ear of the user is determined from a video of the user.

12. A system comprising:
an imaging device configured to capture an image of an external portion of an ear of a user; and
a controller configured to:
store a training set including anthropometric data of a plurality of different users, the anthropometric data for each of the plurality of different users comprising an image of ears of a given user from the plurality of users and a corresponding three-dimensional (3D) geometry of the ears of the given user that describe shapes of external portions of the ears and portions of ear canals of the given user;
train a machine learning algorithm using the training set including the anthropometric data of the plurality of users, the trained machine learning algorithm configured to generate 3D geometries of ears;
receive anthropometric data of the ear of the user, the anthropometric data including the captured image of the external portion of the user that describes the external portion of the ear of the user;
generate a 3D geometry of the ear of the user by applying the anthropometric data within the image of the external portion of the ear to the trained machine learning algorithm, wherein the generated 3D geometry describes a shape of at least a portion of an ear canal of the ear of the user; and
generate a design of an in-ear device based in part on the generated 3D geometry of the ear of the user, the design describing a shell of the in-ear device that is customized to fit within at least a portion of the ear canal of the user.

13. The system of claim 12, wherein the controller is further configured to:
detect, based on the anthropometric data of the user, features of the ear of the user; and
generate, based on the features of the ear of the user, the 3D geometry of the ear of the user.

14. The system of claim 13, wherein the features of the ear of the user include at least one of an entrance of the ear canal of the user, a conchal bowl of the ear of the user, and a pinna of the ear of the user.

15. The system of claim 12, wherein generating the 3D geometry of the ear of the user comprises:
determining features describing the anthropometric data of the user;
identifying key points and detected edges describing the ear of the user using the machine learning algorithm and the features;
compiling the key points and detected edges to form the 3D geometry of the ear of the user.

16. The system of claim 12, wherein at least a portion of the shell of the in-ear device is configured to seal against the ear canal.

17. The system of claim 12, wherein the shell of the in-ear device houses a speaker and an acoustic sensor.

18. The system of claim 12, wherein the design of the in-ear device is provided to a manufacturer of the in-ear device.

19. The system of claim 12, wherein the anthropometric data includes measurements of the ear of the user, and the measurements are used to generate the 3D geometry of the ear of the user.

20. A non-transitory computer readable storage medium comprising computer executable code that when executed by one or more processors causes the one or more processors to perform operations comprising:
storing a training set including anthropometric data of a plurality of different users, the anthropometric data for each of the plurality of different users comprising an image of ears of a given user from the plurality of users and a corresponding three-dimensional (3D) geometry of the ears of the given user that describe shapes of external portions of the ears and portions of ear canals of the given user;
training a machine learning algorithm using the training set including the anthropometric data of the plurality of users, the trained machine learning algorithm configured to generate 3D geometries of ears;
receiving anthropometric data of an ear of a user, the anthropometric data including at least one image describing an external portion of the ear of the user;
generating a 3D geometry of the ear of the user by applying the anthropometric data of the ear of the user that describes an external portion of the ear of the user to the trained machine learning algorithm, wherein the generated 3D geometry describes a shape of at least a portion of an ear canal of the ear of the user; and
generating a design of an in-ear device based in part on the generated 3D geometry of the ear of the user, the design describing a shell of the in-ear device that is customized to fit within at least a portion of the ear canal of the user.

21. The non-transitory computer readable storage medium of claim 20, the one or more processors to perform operations further comprising:
detecting, based on the anthropometric data of the user, features of the ear of the user; and
generating, based on the features of the ear of the user, the 3D geometry of the ear of the user.

* * * * *